United States Patent [19]
Itoh et al.

[11] Patent Number: 5,206,430
[45] Date of Patent: Apr. 27, 1993

[54] METHOD FOR OBTAINING HIGH-PURITY CINNAMIC ACID

[75] Inventors: Hiroyuki Itoh; Yoshitsugu Kono; Ryoichi Taneda, all of Fukuoka; Usaji Takaki, Fujisawa, all of Japan

[73] Assignee: Mitsui Toatsu Chemicals, Incorporated, Tokyo, Japan

[21] Appl. No.: 782,299

[22] Filed: Oct. 24, 1991

[30] Foreign Application Priority Data

Oct. 31, 1990 [JP] Japan .................................. 2-291867
Oct. 31, 1990 [JP] Japan .................................. 2-291868

[51] Int. Cl.$^5$ .............................................. C07C 63/33
[52] U.S. Cl. .................................... 562/494; 562/495; 560/104
[58] Field of Search ................. 562/494, 495; 560/104

[56] References Cited
FOREIGN PATENT DOCUMENTS 0156639  8/1985  Japan .
3506958  8/1985  Japan .

*Primary Examiner*—Paul J. Killos
*Attorney, Agent, or Firm*—Burns, Doane, Swecker & Mathis

[57] ABSTRACT

There is here disclosed a method for obtaining high-purity cinnamic acid containing less metals from crude cinnamic acid containing a metallic catalyst which is a mixture prepared by the synthetic reaction of a cinnamic acid ester. A disclosed purifying means is the combination of alkali hydrolysis, active carbon adsorption, solvent extraction and precipitation with an acid.

4 Claims, No Drawings

METHOD FOR OBTAINING HIGH-PURITY CINNAMIC ACID

BACKGROUND OF THE INVENTION (i) Field of the Invention

The present invention relates to a method for obtaining high-purity cinnamic acid, and more particularly, it relates to a method which can be applied to a crude cinnamic acid derivative-containing mixture formed by reacting a styrene, an alcohol, carbon monoxide and oxygen in the presence of a metallic catalyst in an organic solvent to obtain cinnamic acid having a high purity of 98% or more and containing less metal impurities.

(ii) Description of the Related Art

Cinnamic acid be obtained in the form of its ester from styrene or its derivative, carbon monoxide, an alcohol and oxygen.

As methods for purifying crude cinnamic acid esters, there are a distillation process and a crystallization process which are usual purification methods, but a part of the cinnamic acid ester is inevitably lost in the purifying operation, so that after hydrolysis, the yield of cinnamic acid deteriorates. Additionally, for the purification, expensive distillation facilities and crystallizing/filtering facilities are required.

Even if such a crude cinnamic acid ester is directly subjected to a conventional hydrolysis treatment, cinnamic acid having a high purity and containing less metal impurities cannot be industrially obtained.

Heretofore, various methods for the synthesis of cinnamic acid have been known, but a method has been suggested which comprises reacting styrene or its derivative, carbon monoxide, an alcohol and oxygen in the presence of a catalyst. According to this method, a cinnamic acid ester can be obtained, but a heavy metal which is used as the catalyst is taken into the resultant reaction mixture. Most of the heavy metal is removed from the reaction mixture by filtration, but 10 to 80% of the heavy metal component remains dissolved in the reaction mixture containing the cinnamic acid ester as the main component. In addition, unreacted styrene and by-products are also dissolved in the reaction mixture.

In order to obtain a high-purity cinnamic acid from such a reaction mixture in which the heavy metal, styrene and the by-products are dissolved, a method has been heretofore used which comprises distilling and purifying the reaction mixture to form a high-purity cinnamic acid ester, and then hydrolyzing the formed ester to obtain cinnamic acid. In particular, for the complete removal of the heavy metal from the reaction mixture, the distillation is essential.

However, in the practice of the distillation, expensive distillation facilities are necessary, and tar is formed during the distillation and consequently, some loss of the cinnamic acid ester is unavoidable.

The present inventors have intensively investigated the hydrolysis of the reaction mixture containing the cinnamic acid ester. As a result, they have found that when the crude cinnamic acid ester is directly hydrolyzed without purifying the cinnamic acid ester and the combination of an active carbon treatment and extraction with an organic solvent is then carried out, the high-purity cinnamic acid can be obtained in a high yield. In consequence, the present invention has been completed. Heretofore, the active carbon treatment is effective for the removal of organic compounds and a gas, but there has not been known a method for completely removing the heavy metal by the active carbon treatment, as in the present invention.

SUMMARY OF THE INVENTION

The present inventors have intensively investigated a product obtained by hydrolyzing a reaction mixture containing a cinnamic acid ester with an alkali, and as a result, they have found a method for obtaining cinnamic acid having a high purity and containing less metal impurities in a high yield by directly hydrolyzing a crude cinnamic acid ester without purification, and then carrying out an active carbon treatment and extraction with an organic solvent in combination. In consequence, the present invention has been achieved on the basis of the above-mentioned knowledge.

That is, the present invention is directed to a method for obtaining cinnamic acid having a high purity and containing less metal impurities which comprises reacting a styrene, an alcohol, carbon monoxide and oxygen in the presence of a catalyst in a solvent to form a cinnamic acid ester solution, and then preparing cinnamic acid from the solution, said method being characterized by comprising the steps of subjecting, to an active carbon treatment and an extraction with an aromatic hydrocarbon, an alkane or a cycloalkane in combination, an intermediate formed by hydrolyzing the cinnamic acid ester-containing solution with water and an alkali metal hydroxide to form a cinnamic acid-containing aqueous layer; adding a mineral acid to the aqueous layer to precipitate cinnamic acid; and then filtering and collecting cinnamic acid.

The active carbon treatment is essential in the present invention, and when this treatment is combined with an organic solvent treatment, the purity of the product can be further heightened. Examples of this combination include (a) after the hydrolysis, the active carbon treatment being carried out, (b) after the hydrolysis, the active carbon treatment being carried out, followed by the organic solvent treatment, (c) after the hydrolysis, the organic solvent treatment being carried out, followed by the active carbon treatment, and (d) at the time of the hydrolysis treatment, the active carbon and the organic solvent being allowed to coexist.

DETAILED DESCRIPTION OF THE PREFERRED EMBODIMENTS

A cinnamic acid ester to which a method of the present invention can be applied is a cinnamic acid ester represented by the formula (I)

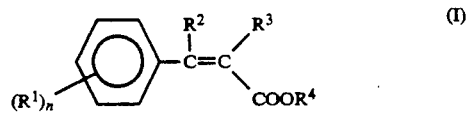

wherein $R^1$ is hydrogen, a halogen, a hydroxyl group, an alkyl group having 1 to 4 carbon atoms or an alkoxy group having 1 to 4 carbon atoms; n is an integer of from 1 to 5; $R^2$ and $R^3$ may be identical or different and each of them is hydrogen or an alkyl group having 1 to 6 carbon atoms; and $R^4$ is an alkyl group or an alkenyl group which may have substituents. Typical examples of the cinnamic acid ester represented by the formula (I) include methyl cinnamate, ethyl cinnamate, propyl cinnamate, butyl cinnamate, ethyl α-methyl-β-phenylacrylate, methyl α-propyl-β-chlorophenylacrylate, methyl β-3,4-dimethoxyphenylacrylate, methyl β-4-methoxyphenylacrylate, benzyl cinnamate, cinnamyl cinnamate and guaiacol cinnamate.

Each of these esters can be obtained by reacting a styrene, an alcohol, carbon monoxide and oxygen in the presence of a catalyst in a solvent, and examples of the catalyst which can be used in this case include catalysts containing, as components, platinum group metals and compounds thereof, compounds of copper and iron, and compounds of metals in the groups IVa, Va and VIIa, the iron group of the group VIIIa, and the groups Ib (except iron) and IIb of the periodic table such as vanadium, manganese, cobalt, nickel and zinc. The reaction solution formed by the above-mentioned reaction contains the solvent and the unreacted alcohol, and therefore it is convenient for the subsequent treatments to remove most of them therefrom by a distillation operation under atmospheric pressure or reduced pressure. Small amounts of the solvent and the alcohol are not particularly influential.

In the above-mentioned ester solution, most of the catalyst used in the reaction precipitates in the form of a solid, and therefore the catalyst can be easily removed from the system by a means such as filtration or centrifugal separation. The thus obtained crude cinnamic acid ester has a purity of from 80 to 90% and the other components are by-products of the reaction.

Prior to the hydrolysis, the reaction solution containing the synthesized cinnamic acid ester is preferably subjected to the distillation, thereby distilling off the solvent and the alcohol so that they will not be present in final products, and the catalyst is preferably separated off by an operation such as filtration. According to these operations, in the subsequent application of the present invention, the amount of the solution to be handled can be decreased to facilitate the operations, and the purity of the final product can be effectively heightened.

In the present invention, the reaction solution containing the crude cinnamic acid ester is then hydrolyzed with an alkali, but usable examples of the alkali include sodium hydroxide and potassium hydroxide. It is desirable from the viewpoint of yield that water is present in an amount necessary to completely dissolve an alkali metal salt of cinnamic acid when the hydrolysis of cinnamic acid ester has completed. Accordingly, the equivalent weight or more of water is added and if necessary, the solution is heated to raise its temperature, and the hydrolysis is then carried out.

Successively, the active carbon is added to the solution, and after mixing, the active carbon is then removed therefrom by the use of a filter. It is not necessary to particularly restrict the kind and shape of active carbon to be used. No particular restriction is similarly put on the amount of the active carbon, but the main function of the active carbon is to adsorb and remove the catalytic component principally comprising metals dissolved in the reaction solution. Therefore, the amount of the active carbon depends upon the amount of the catalytic component which remains in the crude cinnamic acid ester.

Furthermore, an organic solvent is added to the solution which has been subjected to the hydrolysis, and it is then mixed sufficiently to extract impurities. Afterward, the solution is allowed to stand and separate, and the aromatic hydrocarbon, the organic solvent is then removed therefrom. Examples of the organic solvent include aromatic compounds such as benzene, toluene and xylene, and alkanes and cycloalkanes such as normal hexane, heptane and cyclohexane, but the optimal selection of the kind and amount of organic solvent depends upon the kind and concentration of impurities contained in the solution which has been subjected to the hydrolysis. An operation temperature must not be lower than a temperature at which the cinnamic acid ester is dissolved. This extraction permits removing most of the organic by-products formed during the reaction.

The above-mentioned active carbon treatment and organic solvent treatment may be successively carried out after the hydrolysis, or alternatively they may be done simultaneously with the hydrolysis.

In the aqueous phase portion of the solution which has been subjected to these treatments, an alkali metal salt of cinnamic acid is dissolved. Thus, this aqueous phase portion is then separated, and a mineral acid is added thereto in an amount of the equivalent weight or more to liberate and precipitate cinnamic acid, followed by filtering and washing to obtain high-purity cinnamic acid. In this case, when the solution is cooled, the solubility of cinnamic acid can decline to increase the recovery of cinnamic acid. Examples of the mineral acid to be used include hydrochloric acid, sulfuric acid and phosphoric acid. The mineral acid is used in an amount of the equivalent weight or more of the cinnamic acid salt, but after the addition of the mineral acid, the pH of the solution is desirably 2 or less. The yield of cinnamic acid thus obtained is from 97 to 98% with respect to cinnamic acid ester in the crude cinnamic acid ester, its purity is 99.8% or more, and the amount of the metallic components derived from the used catalyst is 5 ppm or less.

The organic solvent treatment and the active carbon treatment may be carried out in converse order. That is, the aromatic hydrocarbon, the alkane or the cycloalkane for extraction is added to the solution which has been subjected to the hydrolysis treatment, and the extraction is then achieved at a predetermined temperature for a necessary period of time, while mixed. The resultant mixture solution is allowed to stand and separate, and the aromatic hydrocarbon, the alkane or the cycloalkane is then removed from the solution. The active carbon is added to and mixed with the obtained aqueous layer and the active carbon treatment is then carried out, followed by filtering to remove the used active carbon from the system. Afterward, the mineral acid is added to the resultant filtrate to precipitate cinnamic acid, followed by filtering and washing to obtain cinnamic acid. In the case of this procedure, the yield and purity of cinnamic acid and the contents of the metals derived from the catalyst are substantially similar to the results of the above-mentioned case.

Moreover, the hydrolysis, the extraction with the solvent and the active carbon treatment can be carried out simultaneously. That is, the aromatic hydrocarbon, the alkane or the cycloalkane for extraction and the active carbon are added to a mixture of the crude cinnamic acid ester, water and the alkali, and the hydrolysis is then achieved at a predetermined temperature for a necessary time, while they are mixed. Afterward, the mixture solution is filtered to remove the active carbon and then allowed to stand and separate, and the aromatic hydrocarbon, the alkane or the cycloalkane is then removed from the system. Next, the mineral acid is added to the resultant aqueous layer to precipitate cinnamic acid, followed by filtering and washing, thereby obtaining cinnamic acid. In the case of this procedure, the yield and purity of cinnamic acid and the contents of the metals derived from the catalyst are substantially similar to the results of the above-mentioned case.

The operations of from the hydrolysis of the crude cinnamic acid ester to the collection of cinnamic acid can be carried out by a batch process or a continuous process. Furthermore, the useful metal components derived from the catalyst are adsorbed on the active carbon removed by the filtration, and these metal components can be recovered therefrom. In consequence, the harmful metal components are inhibited from getting into the cinnamic acid product and the washing waste solution, which is preferable from the viewpoints of safety and sanitation and which can effectively prevent environmental pollution. In the case that the extraction is not carried out and the quality of the cinnamic acid product is maintained only by removing the metallic components derived from the catalyst, the active carbon treatment alone is sufficient. Furthermore, in addition to the above-mentioned active carbon treatment which comprises throwing the above-mentioned powdery active carbon to the treated solution and then removing the same by the filtration, another active carbon treatment can be utilized which comprises packing a column with the active carbon, and then passing the treated solution through the column to adsorb and remove the heavy metal components.

The method of the present invention has the following advantages in contrast to a conventional method which comprises purifying and then hydrolyzing a crude cinnamic acid ester. In addition, the method of the present invention permits obtaining high-purity cinnamic acid with a higher efficiency than the conventional technique.

(1) In the purifying operation of the crude cinnamic acid ester, the loss of the cinnamic acid ester is not present.

(2) Facilities for the purification of the crude cinnamic acid ester are unnecessary.

(3) The quality of cinnamic acid obtained in accordance with the present invention is equal to that of cinnamic acid which can be obtained by hydrolysis after the purification of the crude cinnamic acid ester.

(4) The metallic components derived from the catalyst can be recovered while adsorbed on the active carbon.

Next, the present invention will be described in detail in reference to examples.

Synthesis Example

Synthesis of crude cinnamic acid ester 28.4 mg of palladium chloride, 5.98 g of cupric acetate.monohydrate, 1.34 g of cupric chloride, 12.2 g of manganese acetate.tetrahydrate, 166.65 g of styrene and 256 g of methanol were placed in a glass cylindrical vessel to bring the total amount to 400 ml.

This glass vessel was then inserted into a 1-liter autoclave. The stirring blades of the autoclave were made of Teflon and a temperature measuring pipe was protected with glass. While the total pressure was maintained at 8.5 atm, a gaseous raw material mixture of carbon monoxide, oxygen and carbon dioxide was introduced into the resultant reaction mixture solution with stirring at an inlet flow rate of 4.5 liters/minute (standard condition) and reaction was then carried out at 100° C. for 3 hours, a partial pressure ratio of carbon monoxide:oxygen:carbon dioxide being 12.0:7.0:81.0. During this reaction, an outlet gas was discharged through a reflux condenser.

After completion of the reaction, the same reaction vessel was used, the total pressure was 5.5 atm and the temperature was maintained at 100° C., and in place of the above-mentioned raw material mixed gas, a mixed gas of carbon monoxide and carbon dioxide was introduced into the reaction solution at an inlet flow rate of 4.5 liters/minute (standard condition), followed by stirring for 1 hour, a partial pressure ratio of carbon monoxide:carbon dioxide being 12.9:87.1.

This treated solution was transferred into a flask, and the pressure was slowly reduced at a temperature of from 50° to 80° C. by the use of a rotary evaporator and finally a pressure of 20 mmHg was maintained for 30 minutes to concentrate the solution. Afterward, this concentrated solution, while maintained at 60° C., was filtered through a glass filter under reduced pressure to remove the catalyst therefrom. This synthesis experiment was carried out 5 times, and the filtrates formed in the respective experiments were joined to prepare crude methyl cinnamate which would be used in the subsequent examples and comparative examples. The composition of this crude methyl cinnamate was 87.2% of methyl cinnamate, 2.8% of styrene, 3.2% of acetophenone, 2.2% of dimethyl phenylsuccinate, 0.1% or less of water, 0.1% or less of methanol and 4.5% of other tar components. In addition, the contents of metallic components of palladium, copper and manganese were 5 ppm, 400 ppm and 270 ppm, respectively.

EXAMPLE 1

100 g of crude methyl cinnamate and 926.8 g of 2.8% caustic soda were placed in a 2-liter flask equipped with a thermometer and a stirrer, and the solution was then stirred at 80° C. for 30 minutes to carry out hydrolysis. Furthermore, 1 g of powdery active carbon (trade name PMSX, made by Toyo Calgon Inc.) was added, and the solution was stirred for 30 minutes and then filtered at 80° C. by the use of Nutsche. The resultant filtrate was placed in a 2-liter flask equipped with a thermometer and a stirrer and then maintained at 40° C., and 137.1 g of 25% sulfuric acid was added dropwise to precipitate the crystals of cinnamic acid. After the addition of sulfuric acid had been over, the temperature of the solution was lowered to 20° C., followed by filtering through Nutsche. The resultant filter cake was washed with 1000 g of water, and then vacuum-dried at 50° C. to obtain 86.0 g of cinnamic acid. The purity of cinnamic acid was 98.8%, and the content of each of palladium, copper and manganese was 5 ppm or less. The recovered active carbon was dried, and metallic components were then measured. As a result, the contents of palladium, copper and manganese were 990 ppm, 8.5% and 5.7%, respectively. In the filtrate and the washing solution with which cinnamic acid had been washed, metallic components of palladium, copper and manganese were each contained in an amount of 5 ppm or less.

EXAMPLE 2

100 g of crude methyl cinnamate and 926.8 g of 2.8% caustic soda were placed in a 2-liter flask equipped with a thermometer and a stirrer, and the solution was then stirred at 80° C. for 30 minutes to carry out hydrolysis. Furthermore, the solution which had been subjected to the hydrolysis was passed through a 2.5-cm-diameter, 2.5-cm-high column packed with 25 g of powdery active carbon (Taiko Active Carbon SGA). The thus treated solution was placed in a 2-liter flask equipped with a thermometer and a stirrer and then maintained at 40° C., and 137.1 g of 25% sulfuric acid was added dropwise to precipitate the crystals of cinnamic acid. After the addition of sulfuric acid had been over, the temperature of the solution was lowered to 20° C., followed by filtering through Nutsche. The resultant filter cake was washed with 1000 g of water, and then vacuum-dried at 50° C. to obtain 86.1 g of cinnamic acid. The purity of cinnamic acid was 98.6%, and the content of each of palladium, copper and manganese was 5 ppm or less. In the filtrate and the washing solution with which cinnamic acid had been washed, metallic components of palladium, copper and manganese were each contained in an amount of 5 ppm or less.

EXAMPLE 3

100 g of crude methyl cinnamate and 926.8 g of 2.8% caustic soda were placed in a 2-liter flask equipped with a thermometer and a stirrer, and the solution was then stirred at 80° C. for 30 minutes to carry out hydrolysis. Furthermore, 1 g of powdery active carbon (trade name PMSX, made by Toyo Calgon Inc.) was added, and the solution was stirred for 30 minutes and then filtered at 80° C. by the use of Nutsche. Next, 100 g of toluene was added to the resultant filtrate, and the solution was then stirred at 80° C. for 30 minutes, and after the stop of the stirring, the solution was allowed to stand and separate and the resultant toluene layer was then removed. The resultant aqueous solution was placed in a 2-liter flask equipped with a thermometer and a stirrer and then maintained at 40° C., and 137.1 g of 25% sulfuric acid was added dropwise to precipitate the crystals of cinnamic acid. After the addition of sulfuric acid had been over, the temperature of the solution was lowered to 20° C., followed by filtering through Nutsche. The resultant filter cake was washed with 1000 g of water, and then vacuum-dried at 50° C. to obtain 85.4 g of cinnamic acid. The purity of cinnamic acid was 99.9%, and the content of each of palladium, copper and manganese was 5 ppm or less. The recovered active carbon was dried, and metallic components were then measured. As a result, the contents of palladium, copper and manganese were 880 ppm, 8.6 ppm and 5.8%, respectively. In the filtrate and the washing solution with which cinnamic acid had been washed, metallic components of palladium, copper and manganese were each contained in an amount of 5 ppm or less.

EXAMPLE 4

100 g of crude methyl cinnamate, 926.8 g of 2.8% caustic soda and 100 g of toluene were placed in a 2-liter flask equipped with a thermometer and a stirrer, and the solution was then stirred at 80° C. for 30 minutes to carry out hydrolysis. After the stop of the stirring, the solution was allowed to stand and separate at 80° C. and the resultant toluene layer was then removed. 1 g of powdery active carbon (trade name PMSX, made by Toyo Calgon Inc.) was added to the aqueous layer, and the solution was stirred for 30 minutes and then filtered at 80° C. by the use of Nutsche. The resultant filtrate was placed in a 2-liter flask equipped with a thermometer and a stirrer and then maintained at 40° C., and 137.1 g of 25% sulfuric acid was added dropwise to precipitate the crystals of cinnamic acid. After the addition of sulfuric acid had been over, the temperature of the solution was lowered to 20° C., followed by filtering through Nutsche. The resultant filter cake was washed with 1000 g of water, and then vacuum-dried at 50° C. to obtain 84.9 g of cinnamic acid. The purity of cinnamic acid was 99.9%, and the content of each of palladium, copper and manganese was 5 ppm or less. The recovered active carbon was dried, and metallic components were then measured. As a result, the contents of palladium, copper and manganese were 960 ppm, 8.5% and 5.5%, respectively. In the filtrate and the washing solution with which cinnamic acid had been washed, metallic components of palladium, copper and manganese were each contained in an amount of 5 ppm or less.

EXAMPLE 5

100 g of crude methyl cinnamate, 926.8 g of 2.8% caustic soda, 100 g of toluene and 1 g of powdery active carbon (trade name PMSX, made by Toyo Calgon Inc.) were placed in a 2-liter flask equipped with a thermometer and a stirrer, and the solution was then stirred at 80° C. for 30 minutes to carry out hydrolysis, followed by filtering at 80° C. by the use of Nutsche to remove the used active carbon therefrom. The resultant filtrate was allowed to stand and separate at 80° C. and the resultant toluene layer was then removed. The resultant aqueous layer was placed in a 2-liter flask equipped with a thermometer and a stirrer and then maintained at 40° C., and 137.1 g of 25% sulfuric acid was added dropwise to precipitate the crystals of cinnamic acid. After the addition of sulfuric acid had been over, the temperature of the solution was lowered to 20° C., followed by filtering through Nutsche. The resultant filter cake was washed with 1000 g of water, and then vacuum-dried at 50° C. to obtain 85.1 g of cinnamic acid. The purity of cinnamic acid was 99.9%, and the content of each of palladium, copper and manganese was 5 ppm or less. The recovered active carbon was dried, and metallic components were then measured. As a result, the contents of palladium, copper and manganese were 950 ppm, 8.6 ppm and 5.7%, respectively. In the filtrate and the washing solution with which cinnamic acid had been washed, metallic components of palladium, copper and manganese were each contained in an amount of 5 ppm or less.

COMPARATIVE EXAMPLE 1

100 g of crude methyl cinnamate and 926.8 g of 2.8% caustic soda were placed in a 2-liter flask equipped with a thermometer and a stirrer, and the solution was then stirred at 80° C. for 30 minutes to carry out hydrolysis. An active carbon treatment was omitted. The above-mentioned aqueous solution was maintained at 40° C., and 137.1 g of 25% sulfuric acid was added dropwise to precipitate the crystals of cinnamic acid. After the addition of sulfuric acid had been over, the temperature of the solution was lowered to 20° C., followed by filtering through Nutsche. The resultant filter cake was washed with 1000 g of water, and then vacuum-dried at 50° C. to obtain 87.1 g of cinnamic acid. The purity of cinnamic acid was 96.1%, and the contents of palladium, copper and manganese were 5 ppm or less, 260 ppm, 200 ppm, respectively.

COMPARATIVE EXAMPLE 2

100 g of crude methyl cinnamate and 926.8 g of 2.8% caustic soda were placed in a 2-liter flask equipped with a thermometer and a stirrer, and the solution was then stirred at 80° C. for 30 minutes to carry out hydrolysis. An active carbon treatment was omitted. Then, 100 g of toluene was added to this aqueous solution, followed by stirring at 80° C. for 30 minutes. After the stop of the stirring, the solution was allowed to stand and separate and the resultant toluene layer was then removed. The resultant aqueous layer was placed in a 2-liter flask equipped with a thermometer and a stirrer and then maintained at 40° C., and 137.1 g of 25% sulfuric acid was added dropwise to precipitate the crystals of cinnamic acid. After the addition of sulfuric acid had been over, the temperature of the solution was lowered to 20° C., followed by filtering through Nutsche. The resultant filter cake was washed with 1000 g of water, and then vacuum-dried at 50° C. to obtain 87.6 g of cinnamic acid. The purity of cinnamic acid was 97.4%, and the contents of palladium, copper and manganese were 5 ppm or less, 290 ppm, 240 ppm, respectively.

COMPARATIVE EXAMPLE 3

In the purification experiment of Example 1, a toluene treatment was not carried out after the active carbon treatment of the solution which had been subjected to the hydrolysis. For this reason, Example 1 can be considered to be a comparative example of Example 3.

What is claimed is:

1. A method for obtaining high-purity cinnamic acid from a crude cinnamic acid ester produced by reacting styrene with an alcohol in the presence of a metallic catalyst, said method being characterized by comprising the steps of hydrolyzing the crude cinnamic acid ester in the presence of water in an amount enough to completely dissolve an alkali metal salt of cinnamic acid produced from an alkali metal hydroxide and the cinnamic acid ester; bringing the hydrolyzed material into contact with active carbon and then removing the active carbon to obtain an aqueous phase only; adding a mineral acid as much as the equivalent weight or more of the alkali metal salt of the cinnamic acid contained therein to precipitate a solid; and then separating and collecting the solid.

2. A method for obtaining high-purity cinnamic acid from a crude cinnamic acid ester produced by reacting styrene with an alcohol in the presence of a metallic catalyst, said method being characterized by comprising the steps of hydrolyzing the crude cinnamic acid ester in the presence of water in an amount enough to completely dissolve an alkali metal salt of cinnamic acid produced from an alka metal hydroxide and the cinnamic acid ester; bringing the hydrolyzed material into contact with active carbon and then removing the active carbon to obtain an aqueous phase only; bringing the aqueous phase into contact with an organic solvent and then removing it to obtain the aqueous phase only; adding a mineral acid as much as the equivalent weight or more of the alkali metal salt of the cinnamic acid contained therein to precipitate a solid; and then separating and collecting the solid.

3. A method for obtaining high-purity cinnamic acid from a crude cinnamic acid ester produced by reacting styrene with an alcohol in the presence of a metallic catalyst, said method being characterized by comprising the steps of hydrolyzing the crude cinnamic acid ester in the presence of water in an amount enough to completely dissolve an alkali metal salt of cinnamic acid produced from an alkali metal hydroxide and the cinnamic acid ester; bringing the hydrolyzed material into contact with an organic solvent to obtain an aqueous phase only; bringing the aqueous phase into contact with active carbon and then removing the active carbon to obtain the aqueous phase only; adding a mineral acid as much as the equivalent weight or more of the alkali metal salt of the cinnamic acid contained therein to precipitate a solid; and then separating and collecting the solid.

4. A method for obtaining high-purity cinnamic acid from a crude cinnamic acid ester produced by reacting styrene with an alcohol in the presence of a metallic catalyst, said method being characterized by comprising the steps of hydrolyzing the crude cinnamic acid ester in the presence of an organic solvent, active carbon and water in an amount enough to completely dissolve an alkali metal salt of cinnamic acid produced from an alkali metal hydroxide and the cinnamic acid ester to obtain an aqueous phase only; adding a mineral acid as much as the equivalent weight or more of the alkali metal salt of the cinnamic acid contained therein to precipitate a solid; and then separating and collecting the solid.

* * * * *